United States Patent [19]

Steffen

[11] Patent Number: 5,886,219

[45] Date of Patent: Mar. 23, 1999

[54] PROCESS FOR PREPARING MALONIC ACID AND ALKYLMALONIC ACIDS

[75] Inventor: Klaus-Dieter Steffen, Hennef, Germany

[73] Assignee: Huels Aktiengesellschaft, Marl, Germany

[21] Appl. No.: 19,792

[22] Filed: Feb. 6, 1998

[30] Foreign Application Priority Data

Feb. 6, 1997 [DE] Germany .................. 197 04 449.2

[51] Int. Cl.$^6$ .............................................. C07C 55/08
[52] U.S. Cl. ...................................................... 562/590
[58] Field of Search ............................................ 562/590

[56] References Cited

U.S. PATENT DOCUMENTS

| | | |
|---|---|---|
| 2,373,011 | 4/1945 | Britton and Monroe . |
| 2,391,219 | 12/1945 | Bartlett . |
| 5,041,619 | 8/1991 | von Itter et al. .................. 560/181 |

*Primary Examiner*—Gary Geist
*Assistant Examiner*—Rosalynd Keys
*Attorney, Agent, or Firm*—Oblon, Spivak, McClelland, Maier & Neustadt, P.C.

[57] ABSTRACT

Malonic acid and alkylmalonic acids are prepared by a process of acid-catalyzed saponification of malonic acid esters, which comprises:

contacting an aqueous mixture of the ester II with an acid ion exchanger containing sulfonic acid groups at from 30°–100° C. and from 40–1000 mbar according to the following scheme:

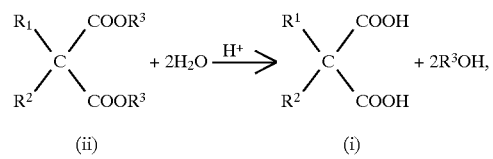

where
$R^1$=H, $CH_3$,
$R^2$=H, $CH_3$ or
$R^1$+$R^2$=—$CH_2$—$CH_2$—and
$R^3$=$CH_3$, $C_2H_5$, $C_3H_7$, $C(CH_3)_3$;

distilling off the alcohol $R^3OH$ which is formed;

separating the water, with the aid of organic solvents, from the malonic acid or alkylmalonic acid product; and then isolating the product by crystallization.

10 Claims, No Drawings

PROCESS FOR PREPARING MALONIC ACID AND ALKYLMALONIC ACIDS

BACKGROUND OF THE INVENTION

1. Field of the Invention

The present invention relates to a process for preparing malonic acid and alkylmalonic acids of formula I

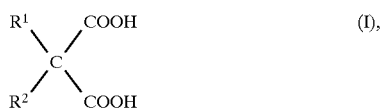

where
$R^1$=H, $CH_3$,
$R^2$=H, $CH_3$ or
$R^1+R^2$=—$CH_2$—$CH_2$—,
by acid catalyzed saponification of the corresponding methyl, ethyl, propyl, isopropyl or tert-butyl esters.

2. Description of the Background

Malonic and alkylmalonic acids are important intermediates in the synthesis of agrochemicals and pharmaceutically active ingredients. They are used, for example, for the preparation of Meldrum's acids, barbiturates, fragrances and vitamins.

The preparation of malonic acid and alkylmalonic acids is described, in general terms, in Kirk-Othmer, Encyclopedia of Chemical Technology, 3rd Edition (1981), Vol. 14, 794–810. Acid or alkaline saponification of esters, nitrites or amides of carboxylic acids can be used. One problem often encountered in the process is that the products are obtained as mixtures with alkali metal salts, e.g. sodium chloride.

Complicating factors in the preparation of malonic acid and alkylmalonic acids are their excellent solubility in water and their ready decarboxylation, which, in the case of malonic acid, begins at temperatures as low as 70° C.

The best-known preparation of malonic acid and also methylmalonic acid starts from chloroacetic acid and α-chloropropionic acid, respectively, which are reacted with sodium cyanide to give the corresponding nitriles, which nitriles are then saponified with sodium hydroxide solution, $NH_3$ being eliminated. According to Organic Syntheses, Vol. II (1943), 376, this procedure is followed by laborious isolation via the Ca salts.

If, after the alkaline saponification of a malonic ester, the malonic acid is present as the alkali metal salt, dissolved in water, the alkali metal cations can be removed, as described in DE 41 20 704, via acid ion exchangers, followed by isolation of the free acid. Since alkaline saponifications always require the use of at least stoichiometric amounts of alkali, which are neutralized again with strong acids in the course of malonic acid work-up, this process produces at least stoichiometric amounts of salt, which often have to be disposed of at considerable expense. This is a major drawback of this method of alkaline saponification.

In acidic saponification of derivatives of malonic acid, inorganic acids are added in catalytic amounts. For example, the saponification of diethyl malonate with sulfuric acid can proceed at 70° C. to give malonic acid, the malonic acid being obtainable from concentrated aqueous solution by crystallization. The drawbacks of the process of acidic saponification are unsatisfactory yields, because of the decomposition of the malonic acids in a strongly acidic environment, and corrosion problems in scaling up of the process.

According to Org. Syntheses, Vol. 60 (1981), 66, cyclopropane-1,1-dicarboxylic acid can be prepared in a yield of about 70% from diethyl malonate, 1,2-dibromoethane, sodium hydroxide solution and stoichiometric amounts of a phase transfer catalyst by simultaneous saponification of the diethyl cyclopropane-1,1-dicarboxylate formed as an intermediate. In addition to the large quantity of phase transfer catalyst, 2.5 times the amount based on the cyclopropane-1,1-dicarboxylic acid obtained, considerable quantities of sodium chloride are also produced which, dissolved in water, require disposal.

Dimethylmalonic acid has likewise been known for a long time and can be prepared by alkaline saponification of the corresponding diethyl ester. Saponification of the dimethyl ester with potassium hydroxide solution to give the acid is mentioned by W. Schauzer, K. Clusius, Z. Physik. Chemie A 190 (1941), 243, without the yield and purity being stated. According to other processes, the acid is obtained by oxidation, employing $KMnO_4$ or $HNO_3$, of methyl precursors. A need, therefore, continues to exist for a method of hydrolyzing malonic ester to prepare malonic acid or malonic acid compounds in good yields with less contamination with salts.

SUMMARY OF THE INVENTION

Accordingly, one object of the present invention is to prepare malonic acid and alkylmalonic acids in good yields in a simple manner without producing troublesome salts, with the process also desirably being environmentally acceptable and readily amenable to scale-up.

Briefly, the object and other objects of the present invention as hereinafter will become more readily apparent can be attained by bringing an aqueous mixture of esters of formula II:

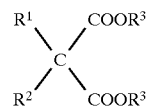

where $R^3$ can be $CH_3$, $C_2H_5$, $C_3H_7$ or $C(CH_3)_3$, into contact with an acid ion exchanger containing sulfonic acid groups at from 30°–100° C. and from 40–1000 mbar, and removing the alcohol formed by distillation, freeing the malonic acid and alkylmalonic acid products obtained from water with the aid of organic solvents, and then obtaining the products in pure form by crystallization.

DETAILED DESCRIPTION OF THE PREFERRED EMBODIMENTS

Only those malonic esters and alkylmalonic esters which contain short alkyl radicals $R^1$ and $R^2$ are suitable for the process. Malonic esters containing higher alkyl groups are saponified too slowly under the conditions employed here and are, therefore, ruled out on economic grounds.

Since the present process requires readily saponifiable esters, groups $R^3$ are likewise restricted to short-chain alkyl groups. The fastest acid-catalyzed saponification is undergone by the methyl esters, whose use in the process is preferred. As a rule they are also the least expensive esters.

The acid catalysts employed are cross-linked polystyrenes which have been sulfonated, of the type commercially available as strongly acid, sulfonyl-containing cation exchangers from various manufacturers, e.g. LEWATIT® S 100 and SP 112 from Bayer A. G., D-51368 Leverkusen.

If the catalyst is introduced directly into the stirred reactor together with the malonic ester or alkylmalonic ester and water, the catalyst beads can to some extent be destroyed mechanically, which may result in poorly filterable fines.

The acid exchanger resins are, therefore, expediently introduced into cylindrical vessels/apparatuses, for example, as columnar shaped sections, and enclosed on both sides (at the top and bottom) by screens, cloths, bonded fiber webs or similar liquid-permeable enclosures. During the reaction the heated, aqueous medium usually flows through them from the bottom upwards, the liberated alcohol distilling off in the process. The aqueous phase containing the dissolved malonic acid or alkylmalonic acid is preferably recirculated and flows back into the heated reactor.

The ion exchange catalyst can be reused any number of times.

Water, generally deionized water, is used for the ester hydrolysis and as the liquid water medium. The ratio of the amounts of ester (II): catalyst: $H_2O$ can vary within very wide limits. Depending on the solubility of the ester in water-at the start of the reaction a two-phase mixture is generally present. The amount of water is increased or reduced. The larger the amount of catalyst, the more rapidly the hydrolysis proceeds.

Because of the thermal lability of the malonic acids, a reaction temperature of from 30°–100° C. at a reduced pressure of from 40–1000 mbar should be set. The reaction is preferably carried out at a temperature from 50°–70° C. and from 100–1000 mbar.

Isolation of the malonic acid and alkylmalonic acids dissolved in water, and the removal of the water with the aid of organic solvents are carried out using two different preferred variants:

1st variant: From 50–95% of the water used originally is removed by distillation. The distillation preferably takes place under reduced pressure at a temperature from 40°–60° C. Then an organic solvent is added in which the malonic acid or the alkylmalonic acid is insoluble, and the remaining water is removed azeotropically. Suitable solvents for this purpose are those which, as the azeotrope, contain relatively large amounts of water, but separate into two phases upon condensation. The aqueous phase is eliminated. Suitable solvents include hydrocarbons and relatively long-chain ethers such as toluene, cyclohexane and dibutyl ether.

The water removed by distillation can be reused in subsequent batches.

The malonic acid and alkylmalonic acids which crystallize from the organic solvent are removed by filtration, washed and dried in vacuo. The filtrate, including the wash liquid of the organic solvent, can be reused for subsequent batches, either directly or after distillation from time to time.

It is especially the recycling of all the solvents that increases the yield, if as yet unhydrolyzed or only monohydrolyzed alkyl malonic esters are present, which are then saponified in subsequent batches to give the corresponding alkylmalonic acids.

2nd Variant: The malonic acid or alkylmalonic acid dissolved in water is extracted with an organic water-immiscible solvent in which, however, the malonic acid or alkylmalonic acid is partially soluble. Because of the good water solubility of the alkylmalonic acids this extraction must be repeated a number of times. Ethers are preferably employed here, especially those having from 4–7 carbon atoms, such as methyl t-butyl ether, diethyl ether, butyl ethyl ether and dipropyl ether. The water thus extracted can be reused directly for subsequent batches. This saves energy for the distillation of water.

The extraction solvent is then largely removed by distillation, residual water also being removed in the process, whereupon the alkylmalonic acid finally crystallizes.

For the purpose of the crystallization, the above-mentioned organic solvent, e.g. ether, in the 2nd variant can also be replaced by a nonsolvent, e.g. toluene, from the 1st variant. This solvent replacement often results in purification and better crystallization of the malonic acid or alkylmalonic acid.

The process is preferably suitable for preparing cyclopropane-1,1-dicarboxylic acid, methyl- and dimethylmalonic acid:

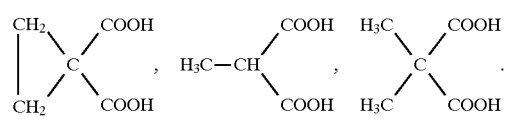

Methylmalonic acid is also known as isosuccinic acid or ethane-1,1-dicarboxylic acid, and dimethylmalonic acid is also known as propane-2,2-dicarboxylic acid.

The purities of the malonic acid and alkylmalonic acids obtained in accordance with the present process are above 99%, and the yields are between 80 and 95% of the theoretical yield.

A byproduct arising from this process is the liberated alcohol, which can be used for some other purpose. Other than that, no salt-like or aqueous wastes are produced. The process is, therefore, environmentally acceptable and readily amenable to scale-up.

The process is also amenable to the use of the monoesters of malonic acid or alkylmalonic acids.

Having generally described this invention, a further understanding can be obtained by reference to certain specific examples which are provided herein for purposes of illustration only and are not intended to be limiting unless otherwise specified.

EXAMPLE 1

Preparation of Cyclopropane-1,1-dicarboxylic acid (CDA)

a) Equipment

A multinecked glass flask with double jacket for heating and bottom drain is connected to the suction side of a hose pump. The discharge side of the pump runs to a glass pipe section containing the catalyst. The glass pipe section opens into the bottom part of the distillation head (including column) fitted onto the multinecked flask.

b) Carrying out the reaction

The glass pipe of the above-described apparatus is charged with 600 ml of the ion exchanger LEWATIT® SP 112 (in the $H^+$ form) and closed on both sides by sintered glass disks. The glass flask contains 500 g of dimethyl cyclopropane-1,1-dicarboxylate (MOD, 98.8%, 3.12 mol) and 750 ml of demineralized water. At a reduced pressure of 700 mbar the contents is heated to boiling (89°–92° C.), the liquids being recirculated by pumping from the flask via the ion exchanger column. At a reflux ratio of from 8:1–15:1 methanol distills off at from 56°–58° C. After 9–10 hours the saponification is complete. After cooling, the apparatus is flushed with water. The combined aqueous solutions are then extracted with 750 ml and twice with 250 ml of methyl t-butyl ether. The ether removed by largely distillation and replaced by 850 ml of toluene. The ether is then removed by distillation completely, and CDA crystallizes in the process. The crystals are removed by filtration, washed with toluene and dried. The final weight and the analytical data are shown in Table 1.

EXAMPLES 2 and 3
Preparation of CDA

The same amounts of MOD are used as in Example 1, and the catalyst, used in Example 1, in the glass pipe is reused. Instead of demineralized water, Example 2 employs the extracted aqueous phase of Example 1, and Example 3 employs the extracted aqueous phase of Example 2. The saponification is carried out as described in Example 1. In Example 2 and Example 3, extraction takes place with the methyl t-butyl ether being removed by distillation in Example 1 and Example 2, respectively (any losses being made up, in each case, with fresh methyl t-butyl ether).

The toluene filtrates from Examples 1 and 2 are distilled and their distillation bottom products (41 g) included in the saponification in Example 3, since they still contain MOD and monomethyl cyclopropane-1,1,1-dicarboxylate (CMA). The toluene distillates are reused every time in the next batches. The results of Examples 2 and 3 are listed in the following Table 1.

TABLE 1

| | CDA | | | | | | | |
|---|---|---|---|---|---|---|---|---|
| Example | Final weight | Yield [% of theo. yield] | M.p. [°C.] | Content titr. | GC analysis [%] | | | $H_2O$ [%] |
| | | | | | CDA | CMA | MCD | |
| 1 | 320 | 77.9 | 138–139 | 99.9 | 98.93 | 0.06 | 0.06 | 0.15 |
| 2 | 360 | 87.4 | 137–138 | 99.3 | 98.65 | 0.11 | 0.06 | 0.31 |
| 3 | 410 | 99.5 | 137–138 | 99.1 | 98.61 | 0.07 | 0.05 | 0.15 |
| Total | 1,090 | 88.4 | Yields all based on 100% purity | | | | | |

EXAMPLE 4
Preparation of CDA

The following are weighed into a multinecked flask fitted with stirrer, distillation head and thermometer: 319.5 g of MCD (99%, 20 mol), 500 ml of demineralized water and 200 ml of ion exchanger LEWATIT® SP 112. At atmospheric pressure the mixture is heated to boiling for 6 hours with stirring and at the same time methanol is removed by distillation at a high reflux ratio of about 20:1. After cooling, the catalyst is removed by filtration via an activated-carbon bed, and 250 ml of toluene are added to the clear filtrate. Under reduced pressure of 200–300 mbar, the water is removed completely as an azeotrope with toluene, and the precipitated CDA crystals are removed by filtration, washed with toluene and dried.

Final weight: 230 g (86.2% of theoretical yield)
Purity (titration) 97.5%
Melting point: 127°–134° C.

EXAMPLE 5
Preparation of Dimethylmalonic acid (DMMA)

The apparatus described in Example 1 is charged with 287 g of dimethyl dimethylmalonate (98%, 1.755 mol), and the bypass is charged with 300 ml of the acid ion exchanger LEWATIT® SP 112 in the H+-active form. The mixture is heated to boiling, and the liberated methanol is removed by distillation at a high reflux ratio of about 15:1. The bottom temperature is 98°–101° C. After 14 h, after 150 g of distillate had been removed, the overhead temperature rises to 98° C. i.e. the reaction is complete.

The ion exchanger is rewashed with fresh water, and the entire aqueous reaction solution is largely boiled down at a reduced pressure of 200 mbar. Towards the end of the distillation, 500 ml of toluene are added, and all of the water is removed by azeotropic distillation. The precipitated crystals are removed by filtration, washed with toluene and dried.

Final weight: 165 g (71.0% of theoretical yield)
Melting point: 189°–190° C. (decomp.)
Content (titration): 99.6%
Content (GC): 99.3%, with residual isobutyric acid.

EXAMPLE 6
Preparation of CDA

A 250 g amount of diethyl cyclopropane-1,1-dicarboxylate (ECD, 1.34 mol) is saponified with 400 ml of demineralized water and 300 ml of ion exchanger LEWATIT® SP 112 (H⁺ form) in 9.5 hours. The reaction is carried out under atmospheric pressure and at a bottom temperature of 98°–100° C. After removal of ethanol by distillation is complete, the mixture is cooled and the aqueous phase is extracted once with 350 ml and three times with 150 ml of methyl t-butyl ether. The ether is largely removed by distillation and replaced by toluene. The precipitated CDA crystals are filtered, washed and dried.

Final weight: 158.5 g (90.7% of theoretical yield)
Melting point: 136°–138° C.

EXAMPLE 7
Preparation of Methylmalonic acid (MMA)

A 443 g amount of dimethyl methylmalonate (99%, 3.0 mol), 600 ml of water and 500 ml of acid ion exchanger LEWATIT® SP 112 are heated in the apparatus described in Example 1, at a reduced pressure of about 500 mbar (bottom temperature about 85° C.). Methanol distills in the process, which is complete after about 7 hours. The apparatus and the catalyst are washed with $H_2O$, and the combined aqueous phases are dewatered azeotropically with 700 ml of toluene under reduced pressure of 500 mbar. The precipitated crystals are filtered, washed and dried.

Final weight: 287 g (81.0% of theoretical yield)
Melting point: 134°–135° C.

EXAMPLE 8
Preparation of Malonic acid (MA)

A 2 liter apparatus with a side glass pipe section containing 400 g of ion exchanger LEWATIT® SP 112 (apparatus as described in Example 1) is charged with 750 ml of demineralized water and 400 g of dimethyl malonate (DMM). The mixture is then circulated over the acid exchanger by pumping and heated to boiling at 200–250 mbar (bottom temperature 65°–70° C.).

In about 12 h, about 200 ml of methanol are removed by distillation, and the reaction solution is then cooled and subjected to a clarification filtration via a sintered glass disk.

Under reduced pressure of 200 mbar, about 500 ml of water are removed by distillation. A 400 g amount of toluene is then added, and the remaining water is removed by azeotropic distillation.

The coarse precipitate of MA crystals is filtered, washed with dry toluene and dried in vacua.

Final weight: 300 g (95.1% of theoretical yield)
Purity: 99.5% (titration, HPLC).

The water removed by distillation and the toluene filtrate are used for the next batch without further purification.

The disclosure of German priority application 197 04 449.2 having a filing date of Feb. 6, 1997, is hereby incorporated by reference into the present application.

Obviously, additional modifications and variations of the present invention are possible in light of the above teachings. It is, therefore, to be understood that within the scope of the appended claims, the invention may be practiced otherwise than as specifically described herein.

What is claimed as new and is desired to be secured by Letters Patent Of The United States is:

1. A process for preparing malonic acid and alkylmalonic acids by acid-catalyzed saponification of malonic acid esters, which comprises:

contacting an aqueous mixture of the ester II with an acid ion exchanger containing sulfonic acid groups at from 30°–100° C. and from 40–1000 mbar according to the following scheme:

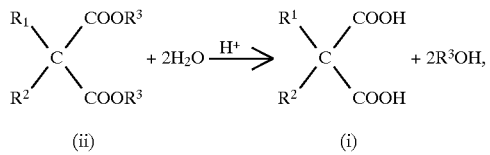

where
$R^1$=H, CH$_3$,
$R^2$=H, CH$_3$ or
$R^1$+$R^2$=—CH$_2$—CH$_2$— and
$R^3$=CH$_3$, C$_2$H$_5$, C$_3$H$_7$, C(CH$_3$)$_3$;

distilling off the alcohol $R^3$OH which is formed;

separating the water, with the aid of organic solvents, from the malonic acid or alkylmalonic acid, product; and then isolating the product by crystallization.

2. The process as claimed in claim 1, wherein $R^3$=CH$_3$.

3. The process as claimed in claim 1, wherein the aqueous mixture of the ester II is passed through a bed of acid ion exchangers containing sulfonic acid groups.

4. The process as claimed in claim 1, wherein the aqueous mixture is treated, at from 50°–70° C. and from 100–1000 mbar, with acid ion exchangers.

5. The process as claimed in claim 1, wherein the water is removed by distillation to from 50–95%, an organic solvent is added and the remaining water is then removed by azeotropic distillation.

6. The process as claimed in claim 5, wherein the organic solvent is toluene, cyclohexane or dibutyl ether.

7. The process as claimed in claim 1, wherein the water is separated by extracting the products with an organic solvent.

8. The process as claimed in claim 1, wherein the extraction is carried out with an ether having from 4–7 carbon atoms.

9. The process as claimed in claim 1, wherein the acid ionic exchanger is a sulfonated polystyrene.

10. The process as claimed in claim 1, wherein the end product of formula (I) is cyclopropane-1,1-dicarboxylic acid, methyl malonic acid or dimethylmalonic acid.

* * * * *